United States Patent
Michal et al.

(10) Patent No.: US 6,221,425 B1
(45) Date of Patent: Apr. 24, 2001

(54) LUBRICIOUS HYDROPHILIC COATING FOR AN INTRACORPOREAL MEDICAL DEVICE

(75) Inventors: Eugene T. Michal, San Francisco; Stephen James Bigus, San Jose, both of CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/016,694

(22) Filed: Jan. 30, 1998

(51) Int. Cl.$^7$ ...................................................... A61L 29/00
(52) U.S. Cl. .................. 427/2.25; 427/2.28; 427/2.3; 427/409; 604/19; 604/317
(58) Field of Search .................................. 427/2.25, 409, 427/2.28, 2.3; 604/19, 317

(56) References Cited

U.S. PATENT DOCUMENTS

| | | |
|---|---|---|
| 3,695,921 | 10/1972 | Shepherd . |
| 3,886,947 | 6/1975 | Sawyer . |
| 3,895,169 | 7/1975 | Wichterle . |
| 4,055,682 | 10/1977 | Merrill . |
| 4,100,309 | 7/1978 | Micklus et al. . |
| 4,111,922 | 9/1978 | Beede et al. . |
| 4,205,018 * | 5/1980 | Nagasawa et al. .................. 427/507 |
| 4,212,901 | 7/1980 | van Neerbos et al. . |
| 4,373,009 | 2/1983 | Winn . |
| 4,459,326 | 7/1984 | Columbo et al. . |
| 4,521,564 | 6/1985 | Solomon et al. . |
| 4,664,658 | 5/1987 | Sawanda et al. . |
| 4,666,437 | 5/1987 | Lambert . |
| 4,714,739 | 12/1987 | Arkles . |
| 4,722,906 | 2/1988 | Guire . |
| 4,729,914 | 3/1988 | Kliment et al. . |
| 4,840,851 * | 6/1989 | Golander et al. .................. 427/385.5 |
| 4,876,126 | 10/1989 | Takamura et al. . |
| 4,906,237 | 3/1990 | Johansson et al. . |

(List continued on next page.)

FOREIGN PATENT DOCUMENTS

| | | |
|---|---|---|
| 0 106 004 | 4/1984 | (EP) . |
| 389 632 | 10/1990 | (EP) . |
| 521 605 | 1/1993 | (EP) . |
| 728 487 | 8/1996 | (EP) . |
| 0 809 997 | 12/1997 | (EP) . |
| 2 064 556 | 6/1981 | (GB) . |
| 2 190 387 | 11/1997 | (GB) . |
| WO 93/11751 | 6/1993 | (WO) . |
| WO 94/26336 | 11/1994 | (WO) . |
| WO 96/23601 | 8/1996 | (WO) . |
| WO 97/46267 | 12/1997 | (WO) . |

*Primary Examiner*—Shrive Beck
*Assistant Examiner*—Bret Chen
(74) *Attorney, Agent, or Firm*—Heller, Ehrman White & McAuliffe LLP

(57) ABSTRACT

A method of providing a lubricious hydrophilic coating on an intracorporeal medical device and the coated device produced thereby, wherein the coating is durable and highly lubricious when in contact with body fluids. In one embodiment, the coating comprises a polymerized base coat and a hydrophilic top coat, where the base coat has a binding component which binds to the hydrophilic compound of the top coat, and a grafting component which binds to the binding component and to the device. In another embodiment, the coating comprises a blend of a hydrophilic compound, a grafting component, and salt, wherein the polymerized grafting component contains uncrosslinked domains. The hydrophilic coating of the invention can be applied to a medical device with a polymeric surface such as a polymeric catheter, or a metal device coated with a polymeric primer.

40 Claims, 3 Drawing Sheets

U.S. PATENT DOCUMENTS

| | | | |
|---|---|---|---|
| 4,911,844 | * 3/1990 | Linder et al. | 210/638 |
| 4,973,493 | 11/1990 | Guire . | |
| 4,978,481 | * 12/1990 | Janssen et al. | 427/302 |
| 4,979,959 | 12/1990 | Guire . | |
| 5,002,582 | 3/1991 | Guire et al. . | |
| 5,023,114 | 6/1991 | Halpern et al. . | |
| 5,026,607 | 6/1991 | Kiezulas . | |
| 5,037,677 | 8/1991 | Halpern et al. . | |
| 5,041,100 | 8/1991 | Rowland et al. . | |
| 5,049,403 | * 9/1991 | Larm et al. | 427/2.1 |
| 5,079,093 | 1/1992 | Akashi et al. . | |
| 5,091,205 | 2/1992 | Fan et al. . | |
| 5,094,876 | 3/1992 | Goldberg et al. . | |
| 5,100,689 | 3/1992 | Goldberg et al. . | |
| 5,135,516 | 8/1992 | Sahatjian et al. . | |
| 5,167,960 | 12/1992 | Ito et al. . | |
| 5,272,012 | 12/1993 | Opolski et al. . | |
| 5,290,548 | 3/1994 | Goldberg et al. . | |
| 5,290,585 | * 3/1994 | Elton | 427/385.5 |
| 5,295,978 | 3/1994 | Fan et al. . | |
| 5,409,731 | * 4/1995 | Nakagawa et al. | 427/2.12 |
| 5,416,131 | 5/1995 | Wolff et al. . | |
| 5,441,488 | 8/1995 | Shimura et al. . | |
| 5,470,307 | 11/1995 | Lindall . | |
| 5,509,899 | 4/1996 | Fan et al. . | |
| 5,603,991 | 2/1997 | Kupiecki et al. . | |
| 5,607,475 | * 3/1997 | Cahalan et al. | 427/2.24 |
| 5,670,558 | 9/1997 | Onishi . | |
| 5,672,638 | * 9/1997 | Verhoeven et al. | 427/2.25 |
| 5,693,034 | 12/1997 | Buscemi et al. . | |
| 5,702,754 | 12/1997 | Zhong . | |
| 5,728,420 | * 3/1998 | Keogh | 427/2.24 |
| 5,756,144 | * 5/1998 | Wolff et al. | 427/409 |
| 5,800,412 | 9/1998 | Zhang et al. . | |
| 5,824,049 | 10/1998 | Ragheb et al. . | |
| 5,840,190 | * 11/1998 | Scholander et al. | 210/500.24 |
| 5,866,113 | * 2/1999 | Hendriks et al. | 427/2.28 |

* cited by examiner

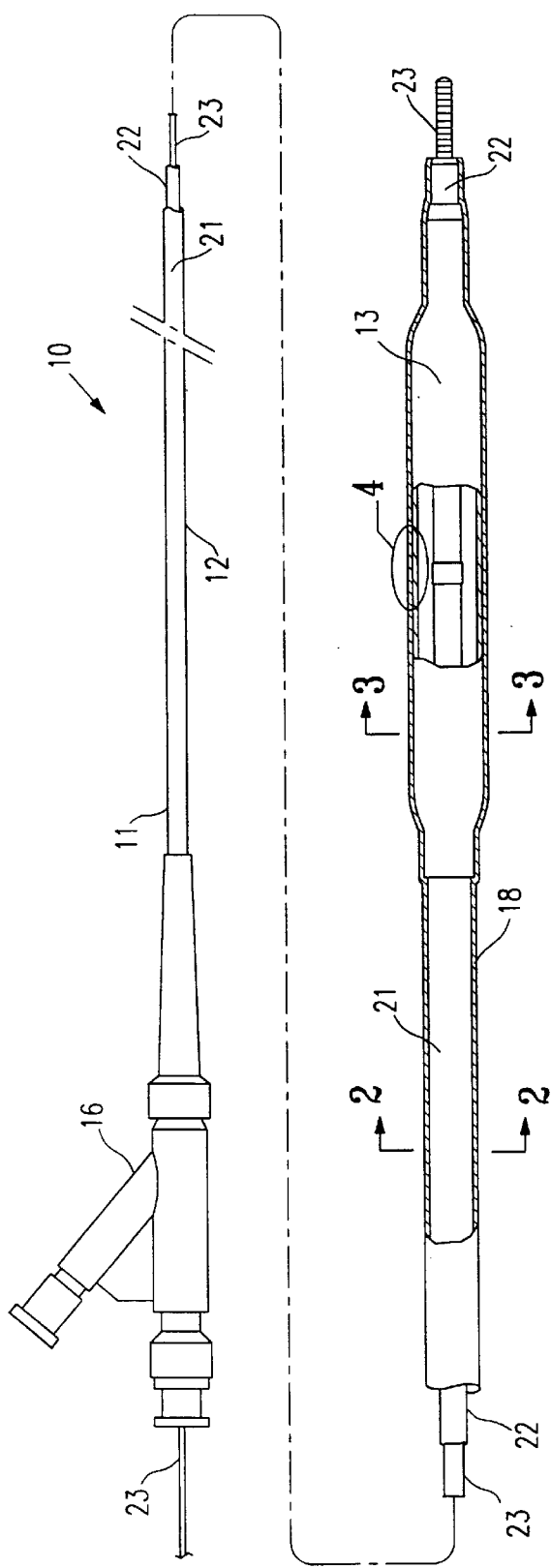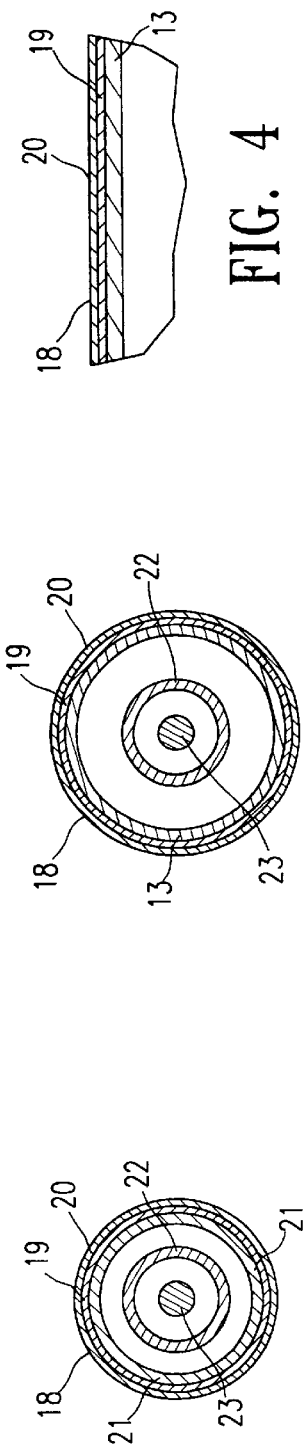

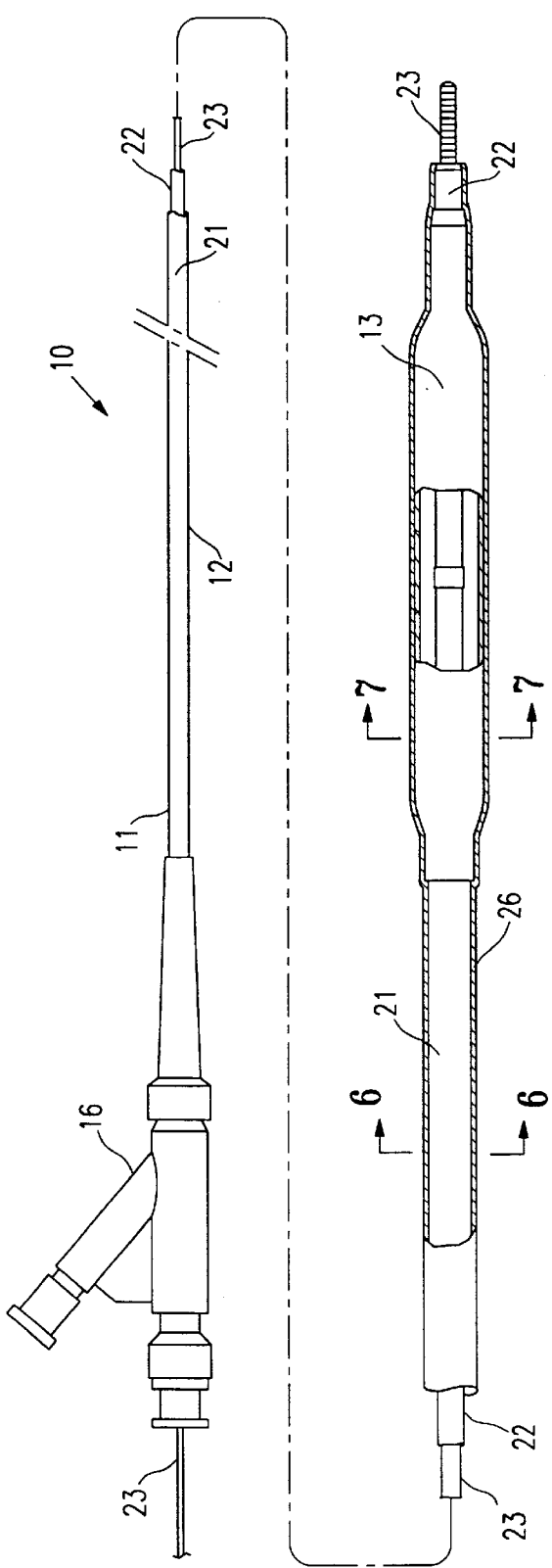
FIG. 5
FIG. 6
FIG. 7

LUBRICIOUS HYDROPHILIC COATING FOR AN INTRACORPOREAL MEDICAL DEVICE

BACKGROUND OF THE INVENTION

This invention relates to the field of lubricious hydrophilic coatings for intracorporeal medical devices, and more particularly to a lubricious hydrophilic coating grafted onto a catheter or onto a guidewire.

The use of a medical devices within a patient may be facilitated by the presence of a lubricious surface on the device. For example, intravascular devices, such as catheters and guidewires, are more easily maneuvered within a patient's vasculature when the friction between the walls of the vessel and the intravascular device is reduced. The friction may be reduced by coating the device with a hydrophilic compound which becomes slippery after adsorbing an appreciable amount of water. Consequently, the hydrophilic coating provides lubricity when the coated device is exposed to aqueous solution, as when the coated device is exposed to water prior to insertion in the patient or to the patient's blood during use. Alternatively, coatings, such as fluoropolymers, and silicone, provide lubricity to the surface of an intracorporeal device without the need for exposure to aqueous solution. However, the degree of lubricity may vary greatly depending on the nature of the lubricious coating. Hydrophilic coatings provide superior lubricity compared to hydrophobic coatings, such as silicone, when tested against a biological tissue countersurface.

In addition to lowering the coefficient of friction of the coated device, an effective lubricious coating must strongly adhere to the device surface. The lubricious coating should remain adhered to the device surface during potentially extended periods of storage, as well as in response to abrasive forces encountered during use. Poor adhesive strength is undesirable because the lost coating may be left behind inside the patient during use, with a corresponding decrease in the lubricity of the device. Typically, a trade off exists between a coating's lubricity and the coating's adhesive and cohesive strength, so that attempts to increase the adhesive strength of lubricious coatings may inadvertently decrease the lubricity of the coating. Consequently, one difficulty has been providing a highly lubricious coating that strongly adheres to a device surface.

It would be a significant advance to provide a hydrophilic coating which strongly adheres to a surface of a medical device to render the device highly lubricious. The present invention satisfies these and other needs.

SUMMARY OF THE INVENTION

The invention is directed to a method of providing a lubricious hydrophilic coating on an intracorporeal medical device, and the coated medical device produced thereby. A durable hydrophilic coating is provided on the medical device, which is highly lubricious when in contact with body fluids.

In one embodiment, the hydrophilic coating on the intracorporeal medical device generally includes a base coat and a lubricious hydrophilic top coat. The base coat has a binding component and a grafting component, and is used to strongly bind the hydrophilic top coat to the medical device. Specifically, the binding component binds to both the hydrophilic polymer and to the grafting component, and the grafting component grafts to the device surface. In the method of providing a lubricious hydrophilic coating on a device, the device is first coated with a solution which contains both the grafting component and the binding component. The coated device is then exposed to polymerizing radiation to polymerize the grafting component and form a base coat on the device. The device is then coated with a solution of the hydrophilic top coat, and the coated device allowed to dry, to form a hydrophilic coating on the device. Because the top coat bonds to the base coat during drying, the hydrophilic coating produced will not readily wear off, even after repeated hydration and abrasion.

In another embodiment, a base coat is not used, and the hydrophilic coating on the intracorporeal medical device generally includes a hydrophilic polymer, an ionic compound with at least one inorganic ion, and a grafting component. The grafting component is polymerized as outlined above, so that the grafting component grafts to the device and crosslinks to the hydrophilic polymer, to form a hydrophilic coating on the device. When the coated device is hydrated, the coating absorbs water and is highly lubricious, but does not dissolve in the aqueous or blood medium because the hydrophilic polymer is immobilized by the grafted network. Moreover, the ionic compound, or salt, increases the lubricity of the hydrophilic coating by providing uncrosslinked domains in the crosslinked matrix. Because the ability of a hydrophilic polymer to absorb water is decreased when the polymer is crosslinked, the salt enhances the polymer lubricity by disrupting the crosslinking of the hydrophilic polymer into the grafting component crosslinked network. Therefore, when the hydrophilic coating is hydrated by exposure to a solvent and the salt dissolves, these uncrosslinked domains provide additional lubricity by increasing the contact between the hydrophilic polymer and the countersurface, e.g. the patient's vessel wall, and hence additional lubricity.

To hydrate the hydrophilic coating on the device and render the coating highly lubricious, the coated device may be exposed to aqueous fluid either before insertion into a patient or by contact with body fluid while inside the patient.

The hydrophilic coating of the invention can be applied to any device having a polymeric surface, as for example, a catheter formed of conventional materials. For example, the catheter components may be formed of high density polyethylene, polyethylene terephthalate, and polyolephinic ionomers such as Surlyn®), nylon and the like which are frequently used to form dilatation balloons or catheter shafts. Additionally, the device may be a metal device, such as a metal guidewire, that has been coated with a polymeric primer coating to produce a polymeric surface.

The coated device of the invention has a superior hydrophilic coating which is highly lubricious against biological tissue and is strongly bound to the device surface due to the grafting component used alone or in combination with the binding component. In the case of a PTCA catheter or guidewire, the coating serves to enhance device access to distal lesions and the ease with which a device crosses small diameter athlerosclerotic lesions. These and other advantages of the invention will become more apparent from the following detailed description of the invention and the accompanying exemplary drawings.

BRIEF DESCRIPTION OF THE DRAWINGS

FIG. 1 is an elevational view, partially in section, of a dilatation catheter having a hydrophilic coating of the invention.

FIGS. 2 and 3 are transverse cross sections of the catheter shown in FIG. 1 taken along lines 2—2 and 3—3, respectively.

FIG. 4 is an enlarged longitudinal cross-sectional view of the coated catheter shown in FIG. 1 within the circle 4.

FIG. 5 is an elevational view, partially in section, of a dilatation catheter having a hydrophilic coating of the invention.

FIGS. 6 and 7 are transverse cross sections of the catheter shown in FIG. 5 taken along lines 6—6 and 7—7, respectively.

DETAILED DESCRIPTION OF THE INVENTION

Figure 8:
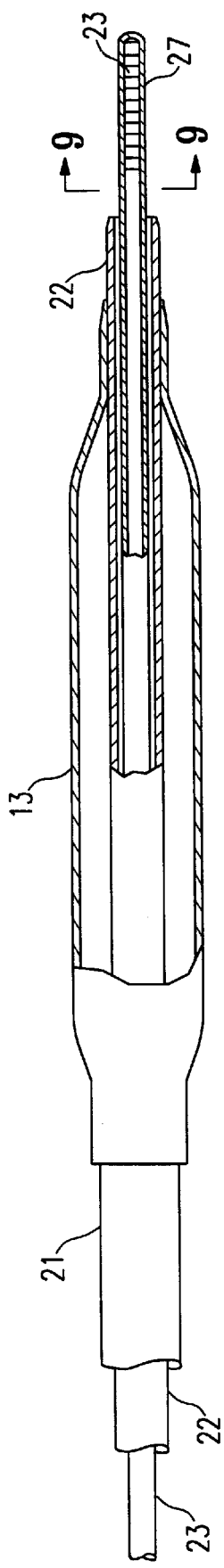
FIG. 8 is a longitudinal cross section of a guidewire having a hydrophilic coating of the invention.

In one embodiment of the invention, shown in FIG. 1, the intracorporeal medical device having a lubricious coating of the invention 10 is a dilatation catheter 11, generally including an elongated catheter shaft 12, with an inflatable dilatation balloon 13 on the distal end and an adapter mounted 16 on the proximal end. The catheter shaft 11 and balloon 13 are coated with a lubricious hydrophilic coating 18. As best shown in FIG. 4, illustrating an enlarged longitudinal cross section of the coating shown in FIG. 1 within circle 4, the coating 18 comprises a base coat 19 and a top coat 20. FIGS. 2 and 3 illustrate a transverse cross section of the catheter of FIG. 1 taken along lines 2—2 and 3—3, respectively. The catheter shaft may comprise an outer tubular member 21, and an inner tubular member 22 disposed in a lumen of the outer tubular member and having a lumen configured to slidably receive a guidewire 23.

In the embodiment illustrated in FIGS. 1–4 in which the hydrophilic coating comprises a base coat 19 and a top coat 20, the base coat has a grafting component and a binding component. The grafting component is selected from the group consisting of vinyl compounds, acrylate compounds, and allyl compounds, such as any oligomer or monomer with one or more vinyl, acrylate or allyl double bonds. Exemplary of the vinyl compounds are di-vinyl benzene, n-vinyl pyrrolidone, and triethylene glycol divinyl ether. Exemplary of the acrylate compounds are tri-methylol propane tri-acrylate, pentaerythritol tetra-acrylate, and Bisphenol A. ethoxylate diacrylate. Exemplary of the allyl compounds are allyl ether, di-allyl maleate, and tri-allyl isocyanurate.

To form the base coat 19, the grafting component is blended with a binding component, with the nature of the binding component varying depending on the identity of the hydrophilic top coat 20 that will be applied thereto. The binding component and hydrophilic compound have functional groups capable of binding to one another, so that the hydrophilic compound will be securely bound to the medical device through covalent attachment to the binding component. In one embodiment, the binding component is selected from the group consisting of polyaziridine and polycarbodiimide resin compounds, and the top coat is a hydrophilic polymer having carboxyl groups capable of binding to the binding component. Exemplary of the polyaziridine compounds are tri-aziridine oligomer, such as Zeneca cs-100 available from Zeneca Resins. Exemplary of the carbodiimide compounds are XL-29SE available from Union Carbide. The hydrophilic compound is a polymer showing appreciable water absorption and containing carboxyl groups, including but not limited to, polyacrylic acid, alginic acid, carboxy methyl cellulose, and hyaluronic acid.

In another embodiment, the binding component comprises an aldehyde compound and the top coat is a hydrophilic compound having amine groups. Exemplary of such aldehyde compounds are glutaraldehyde, cinnamaldehyde, and acrolein. Exemplary of the hydrophilic compound are a (co)monomer selected from the group consisting of 2-aminoethyl acrylate, 2-aminoethyl methacrylate, and N-(3-aminopropyl)methacrylamide; or a polymer of at least one of said (co)monomers co-polymerized with hydrophilic monomers selected from the group consisting of acrylamide, di-methyl acrylamide, and N-vinyl pyrrolidone; or a peptide having a secondary basic group for reaction with the aldehyde of the binding component, such as arginine, glutamine, and histidine, which include but are not limited to gelatin, hirudin, and albumin; or polyethylenimine.

In another embodiment, the binding component is an isocyanate compound and the top coat is a compound showing appreciable water absorption and containing hydroxy or amine groups. Exemplary of such isocyanate compounds are an aliphatic or aromatic isocyanate monomer, biuret or isocyanurate oligomer, or polyol or polyamine chain extended variant of such starting materials as 1,6 hexamethylene diisocyanate, isophorone diisocyanate, toluene diisocyanate, diphenylmethanediisocyanate, bis(4-isocyanato cyclohexyl) methane. The isocyanate compound can also be the monomer or polymer made from allyl isocyanate or other such monomers. Exemplary of the hydrophilic compound are poly(vinyl alcohol), hydroxy propyl cellulose, hyaluronic acid, a peptide having a secondary basic group for reaction with the isocyanate of the binding component, and a copolymer blend of a first monomer selected from the group consisting of vinyl and acrylic monomers and a second monomer selected from the group consisting of hydroxy and amine monomers. Examples of the peptide include but are not limited to gelatin, hirudin, and albumin, and examples of the copolymer blend hydrophilic polymers include but are not limited to an 80/20 mixture of acrylamide and hydroxy ethyl methacrylate.

In the embodiment illustrated in FIGS. 1–4, in which the hydrophilic coating 18 comprises a top coat 20 on a base coat 19 having a binding and a grafting component, the method of providing a lubricious hydrophilic coating on an intracorporeal medical device of the invention comprises, applying to the medical device a solution having a binding component and a grafting component, and polymerizing the grafting component so that the grafting component grafts to the device and crosslinks with the binding component, to form the base coat 19. The device thus coated with the base coat 19, hereafter the base coated device, may typically be dried, either a room temperature or at elevated temperatures, to evaporate the base coat solution solvent, before polymerizing the grafting component. The base coat on the device is then coated with a solution of a hydrophilic compound to form the top coat 20. The coated device is then dried, at elevated or room temperature, so that the hydrophilic polymer grafts via covalent bonds to the binding component, to form the hydrophilic coating 18 on the device. The coating 18 can then be hydrated by exposure to aqueous solution, rendering it highly lubricious.

In the embodiment in which the hydrophilic compound functional groups are carboxyl groups, the hydrophilic coating may be exposed to a basic solution, such as 0.1 N potassium or sodium hydroxide, to neutralize free carboxyl groups on the hydrophilic coating. The coating is then rinsed in water to remove the basic solution.

Polymerization of the grafting component is carried out by irradiating the base coated device with ultra-violet (UV) light or with electron beam irradiation. When UV light is used, photoinitiators must be present in the base coat solution. In the process of polymerization, the UV light induces free radicals on the photoinitiators, which transfer to the acrylate, vinyl or allyl compound of the grafting component, thereby causing the grafting component to polymerize into a crosslinked network. These processes, involving UV or electron beam irradiation, are known in the art as radiation induced acrylate/vinyl free radical polymerization. Additionally, during this process, the acrylate, vinyl or allyl network crosslinks to the functional groups of the binding component, e.g. the polyaziridine or polycarbodiimide oligomers, the isocyanate containing oligomer, or the aldehyde or polyaldehyde compound, and grafts to the device polymeric surface via a hydrogen abstraction mechanism. The result is a well adhered base coat 19 containing free unreacted binding component functional groups on the surface of the coating available to graft the hydrophilic compound of the top coat 20.

The photoinitiator is any compound that generates a free radical when irradiated with UV or visible light. Exemplary of the photoinitiator are benzophenone, benzoin methyl ether, 2,2 dimethoxy-2-phenylacetophenone, 1-hydroxycyclohexyl phenyl ketone, and ethyl 4-(dimethylamino)benzoate.

FIG. 5 illustrates another embodiment of the invention, in which the binding component is omitted, and the coating 26 comprises a grafting component blended with the hydrophilic compound before being applied to the device. FIGS. 6 and 7 illustrate transverse cross sections of the coated catheter shown in FIG. 5. In this embodiment of the invention, the method of providing a lubricious hydrophilic coating on an intracorporeal medical device comprises applying to the device a solution comprising a hydrophilic polymer, an ionic compound with at least one inorganic ion, and a grafting component. The grafting component is polymerized so that the grafting component grafts to the device and crosslinks with the hydrophilic polymer, with some uncrosslinked domains remaining in the crosslinked matrix. The coated device is typically dried before exposure to the polymerizing radiation. The coated device can then be hydrated by exposure to an aqueous solution, whereby the hydrophilic polymer absorbs the solution and the salt dissolves, rendering the coating highly lubricious.

In the embodiment illustrated in FIG. 5 the hydrophilic compound is any polymer displaying appreciable water absorption, including but not limited to poly(ethylene oxide), poly(vinylpyrrolidone), poly(vinyl alcohol), poly (acrylamide), alginic acid, hyaluronic acid, poly(acrylic acid), and guar gum. The grafting component and its polymerization are as discussed in the previous embodiments. Suitable ionic compounds with at least 1 inorganic ion, i.e. a salt, include but are not limited to potassium bromide, and sodium chloride.

Figure 9:
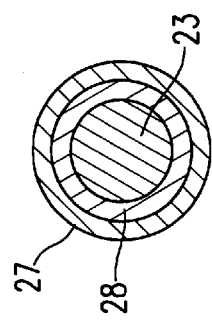
FIG. 9 is a transverse cross section of the guidewire shown in FIG. 8 taken along lines 8—8.

In another aspect of the invention in which the medical device is formed of metal, a primer coating is applied to the device before applying the hydrophilic coating. FIG. 8 illustrates a metal guidewire 23 having a primer coat 28 and a lubricious hydrophilic coating 27 of the invention. The primer coat 28 is applied to at least the entire length of the guidewire to be coated with the hydrophilic coating. The polymerized primer coating 28 is selected from the group consisting of vinyl, acrylate and allyl compounds. The vinyl or acrylate compounds of the primer and the polymerization of these compounds are as discussed above for the grafting components. FIG. 9 illustrates a transverse cross section of the guidewire shown in FIG. 8 along lines 9—9. In the presently preferred embodiment illustrated in FIG. 8, the hydrophilic coating 27 is the same as coating 26, comprising a grafting component blended directly with a hydrophilic compound and an ionic compound with at least one inorganic ion. However, the hydrophilic coating 27 may comprise the hydrophilic coating 18 having a base coat 19 and top coat 20 as discussed above. In the method of the invention, a solution comprising the primer coating is applied to the guidewire 23, and primer coat 28 is typically dried before the vinyl or acrylate compound is polymerized. A solution comprising the hydrophilic compound and grafting component is then applied to the primer coat and exposed to polymerizing radiation, to form the hydrophilic coating 27 on the guidewire.

The presently preferred method of coating the device with the coating(s) is by dip coating at a given rate. However, the device may be coated by numerous suitable methods, including but not limited to, spray coating, wipe coating, or other techniques known in the art. Many suitable solvents may be used in the coating solutions including but not limited to water, alcohols, and ketones.

In the presently preferred embodiments, the device is a polymeric catheter, or a metal guidewire coated with a primer. However, the device can be any intracorporeal medical device in which a reduction of friction or modification of the surface absorption properties is desired. The surface of the device is generally cleaned before coating with the primer or the hydrophilic coating solutions, and may optionally be plasma treated to improve coating adhesion.

In a presently preferred embodiment, illustrated in FIGS. 1 and 5, the lubricious hydrophilic coating 18, 26 on a dilatation catheter covers the outer surfaces of both the catheter shaft and balloon. However, the coating may be applied to various catheter surfaces, including an inner surface of the catheter to facilitate displacement of objects, such as a guidewire, within a lumen of the catheter, or an outer surface of the inner tubular member 22. Also, the hydrophilic coating 18, 26, 27 may be applied to less than the entire outer surface of the device, as when a proximal portion of the catheter or guidewire is left uncoated to provide a handling location, or when the balloon is left uncoated to provide frictional engagement with the patient when the balloon is inflated. For example, in a typical balloon angioplasty catheter of 144 cm, the coating 18, 26 would be applied to about 2 cm to about 105 cm of the catheter. When the device is a guidewire, the coating 27 would be applied to about 2 cm to about 40 cm of the total guidewire length of 175 cm.

The following examples more specifically illustrate the invention. The percent values for the coating components is a percent by weight of the total formula weight.

EXAMPLE 1

Formula for Lubricious Hydrophilic Coatings Having a Base Coat and a Hydrophilic Top Coat

| Coating Layer | Component | % of Non-Volatile | % of Total Formula |
|---|---|---|---|
| Lubricious Hydrophilic Coating Formula I: | | | |
| Base coat | 1. Binding component: polyaziridine or | 5–70% | |

-continued

Formula for Lubricious Hydrophilic Coatings Having a Base Coat and a Hydrophilic Top Coat

| Coating Layer | Component | % of Non-Volatile | % of Total Formula |
|---|---|---|---|
| | polycarbodiimide compound | | |
| | 2. Grafting component: vinyl or acrylic functional monomer/ oligomer | 10–95% | |
| | 3. Photoinitiators | 0.05–10% | |
| | 4. Solvents | N/A | 40–99% |
| Top coat | 1. Hydrophilic compound: carboxyl containing polymer | | 0.05–15% |
| | 2. Solvents | | 84–99.5% |
| | 3. Amine or base | | 0–5% |
| Lubricious Hydrophilic Coating Formula II: | | | |
| Base coat | 1. Binding component: isocyanate functional monomer/ oligomer/polymer | 5–90% | |
| | 2. Grafting component: vinyl or acrylic functional monomer/ oligomer | 5–95% | |
| | 3. Isocyanate catalyst | 0–2% | |
| | 4. Photoinitiators | 0.05–10% | |
| | 5. Solvents | N/A | 40–99% |
| Top coat | 1. Hydrophilic compound: hydroxy or amine containing polymer | | 0.05–20% |
| | 2. Solvents | | 80–99.5% |
| Lubricious Hydrophilic Coating Formula III: | | | |
| Base coat | 1. Binding component: aldehyde compound | 5–90% | |
| | 2. Grafting component: vinyl or acrylic functional monomer/ oligomer | 5–90% | |
| | 3. Photoinitiators | 0–10% | |
| | 4. Solvents | N/A | 40–99% |
| Top coat | 1. Hydrophilic compound: amine containing polymer | | 0.01–20% |
| | 2. Solvents | | 80–99.9% |

EXAMPLE 2

Device Coated with a Base Coat and a Hydrophilic Top Coat of Formula I

A base coat comprising 0.5 grams (gm) tri-aziridine oligomer (Zeneca cx-100), 1.5 gm trimethylol propane tri-acrylate, with an intermediate chain extension of 200 molecular weight (mol. wgt.) PEG (Henkel Photomer 4158), 0.004 gm benzophenone and 0.004 gm. 2,2 dimethoxy-2-phenylacetophenone, in 17.9 gm n-butyl acetate was applied to a coronary dilatation catheter that had been chemically cleaned and plasma treated by dip coating the catheter in a base coat solution at 20 inches per minute. The base coated device was dried for 20 seconds at 110° F., then irradiated in front of a Fusion Systems, "H" Bulb, ultra-violet source for 20 seconds at a minimum intensity of 50 milliwatts per square centimeter. A top coat of 1.5 gm poly(acrylic acid) (mol. wgt. 250K), 99 gm water, 25 gm 2-propanol, and 0.5 gm 28% $NH_3$ to increase acrylic acid solubility, was then applied by dip coating the base coated device in a top coat solution at 20 inches per minute. The coated device was then dried in a convection oven at 55° C. for 15 minutes. The dried coated device was then dipped in 0.1 N KOH, and rinsed freely with water, to neutralize any free carboxyl groups on the hydrophilic polymer to increase the hydrophilic character of the topcoat and enhance its lubricity. The resulting catheter having a lubricious hydrophilic coating is extremely lubricious when wet, and the coating showed resistance to wearing off. If rubbed repeatedly under running water and then tested for lubricity against an excised porcine aorta counter surface, the catheter had a coefficient of friction of 0.08. A similar unit without the basecoat of the invention had a coefficient of friction of 0.32, which is equivalent to an uncoated catheter.

EXAMPLE 3

Device Coated with a Base Coat and a Hydrophilic Top Coat of Formula II/III

The procedure outlined above in Example 2 was performed using lubricious hydrophilic coatings from the class of coatings labeled "Formula II" and "Formula III" in Example 1, except that the dried coated device is not dipped in a basic neutralizing solution. Thus, the base coat was applied to a coronary dilatation catheter that was chemically cleaned and plasma treated, by dip coating at 20 inches/min. The base coated catheter was then dried for 20 seconds at 110° F., and then irradiated in front of an ultra-violet source (Fusion Systems, "H" Bulb) for 20 sec. at a minimum intensity of 50 milliwatts per square centimeter. The top coat was then applied by dip coating at 20 in./min., and the coated catheter was baked in a convection oven at 55° C. for 15 min. The resulting catheter having a lubricious hydrophilic coating is extremely lubricious when wet, and the coating showed resistance to wearing off.

The specific coatings used were as follows:

For Formula II, the base coat was 1.5 gm isocyanurate trimer of 1,6 hexamethylene diisocyanate (Bayer Desmodur N-3300), 0.5 gm trimethylol propane tri-acrylate, with an intermediate chain extension of 200 mol. wgt. PEG (Henkel Photomer 4158), 0.004 gm benzophenone, 0.004 gm 2,2 dimethoxy-2-phenylacetophenone, 0.0005 gm dibutyl tin dilaurate, and 17.9 gm n-butyl acetate, and the top coat was 2.0 gm poly(vinyl alcohol) (mol. wgt. 100K), and 98.0 gm water.

For Formula III, the base coat was 2.0 gm of glutaraldehyde (25% in water), 1.5 gm trimethylol propane tri-acrylate, with an intermediate chain extension of 200 mol. wgt. PEG (Henkel Photomer 4158), 0.004 gm benzophenone, 0.004 gm 2,2 dimethoxy-2-phenylacetophenone, and 17.9 gm 2-propanol, and the top coat was 2.0 gm gelatin (175 bloom, swine skin, Aldrich Chemical Co.), and 98.0 gm water.

EXAMPLE 4

Formula for Lubricious Hydrophilic Coating Having a Blend of a Grafting Component and a Hydrophilic Top Coat

| Component | % of Non-Volatile | % of Total Formula |
|---|---|---|
| 1. Grafting component: vinyl or acrylic functional monomer/oligomer | 5–45% | |
| 2. Hydrophilic compound | 50–95% | |
| 3. Salt | 0.1–40% | |

-continued

| Formula for Lubricious Hydrophilic Coating Having a Blend of a Grafting Component and a Hydrophilic Top Coat | | |
| --- | --- | --- |
| Component | % of Non-Volatile | % of Total Formula |
| 4. Photoinitiators | 0.0–10% | |
| 5. Solvents | N/A | 80–99.9% |

1.36 gm of trimethylol propane triacrylate with an intermediate chain extension of 200 mol. wgt. PEG (Henkel Photomer 4158), 0.018 gm benzophenone and 0.018 gm 2,2 dimethoxy-2-phenylacetophenone were dissolved in 30 gms 2-propanol. The solution was then added to 653 gm 2-propanol in a container equipped with a stirrer. With agitation, 7.5 gms poly(ethylene oxide), 1 million mol. wgt, was added. 1.5 gms potassium bromide was dissolved in 116 gms water, and added to above. This solution was stirred until poly(ethylene oxide) was fully dissolved, about 1 hour.

The coating was applied to a coronary dilatation catheter that was chemically cleaned and plasma treated, by dip coating at 20 in./min. The coated catheter was dried for 20 sec. at 110° F., and then UV irradiate as outlined above. When evaluated in a friction test using excised porcine aorta as a countersurface, the hydrophilic coating yields an average force of 31 gm, as opposed to 98 gm for a control silicone coating, for a 68% reduction in force.

EXAMPLE 5

| Formula for Primer Coating and Lubricious Hydrophilic Coatings for Coating A Metal Device | | | | |
| --- | --- | --- | --- | --- |
| Coating Layer | Component | | % of Non-Volatile | % of Total Formula |
| Primer coat | 1. | Vinyl or acrylate containing monomer or oligomer | 90–100% | |
| | 2. | Photoinitiators | 0–10% | |
| | 3. | Solvents | N/A | 60–99% |
| Hydrophilic coating blend | 1. | Grafting component: vinyl or acrylic functional monomer/oligomer | 5–49% | |
| | 2. | Hydrophilic compound | 50–95% | |
| | 3. | Salt | 0.1–40% | |
| | 4. | Photoinitiators | 0.0–10% | |
| | 5. | Solvents | N/A | 80–99.9% |

In 100 gm of ethyl acetate, was dissolved 0.05 gm benzophenone, 0.05 gm 2,2 dimethoxy-2-phenylacetophenone, and 20 gm bisphenol A ethoxylate diacrylate (Henkel Photomer 4028). The primer was applied to a chemically cleaned guidewire by dip coating at 20 in/min, and dried for 15 sec. at 100° F., and irradiated with UV source (Fusion Systems, "H", Bulb) for 25 sec. at minimum intensity of 50 milliwatts/cm$^2$. For the hydrophilic coating, 0.84 gm trimethylol propane triacrylate, 0.018 gm benzophenone and 0.018 gm 2,2 dimethoxy-2-phenylacetophenone was dissolved in 30 gms 2-propanol. It was added to 650 gm 2-propanol in a container equipped with a stirrer. With agitation, 7.5 gms poly(ethylene oxide), 1 million mol. wgt, was added. 0.4 gm potassium bromide was dissolved in 116 gms water and added to above. The mixture was stirred until poly(ethylene oxide) was fully dissolved, about 1 hour. The top coat was applied to the primed guidewire by dipping, drying, and then irradiating as outlined for the primer coat.

The guidewire thus coated has a durable lubricious coating when wet, resulting in a coefficient of friction of 0.03, compared to a coefficient of friction of 0.18 for a silicone coating. The hydrophilic coating was found to slough off rapidly when wet if the primer coat was omitted.

Although the invention has been described herein in terms of certain preferred embodiments, modifications and improvements thereof may be made without departing from the scope of the invention.

What is claimed is:

1. A method of providing a coating for an intracorporeal medical device, comprising:
    a) applying to the medical device a solution having a grafting component and a binding component, wherein the grafting component is selected from the group consisting of vinyl, acrylate and allyl compounds, and the binding component is selected from the group consisting of polyaziridine resin compounds, polycarbodiimide resin compounds, aldehyde compounds, and isocyanate compounds;
    b) polymerizing the grafting component in the presence of the binding component by irradiating the grafting component with radiation, and bonding the grafting component to the binding component, to form a base coat on the device; and
    c) applying to the base coat a solution of a top coat compound having a functional group capable of bonding to the binding component, so that the top coat compound bonds to the binding component, to form the coating on the medical device.

2. The method of claim 1 wherein the top coat compound is a hydrophilic compound having functional groups selected from the group consisting of carboxy, hydroxy, and amine groups, and including the step of drying the coated medical device after at least one of the solutions of the grafting and binding components or the hydrophilic compound are applied to the medical device.

3. The method of claim 2 including hydrating the hydrophilic coating on the medical device to form a lubricious hydrophilic coating.

4. The method of claim 1 wherein polymerizing the grafting component comprisings irradiating the grafting component with ultra-violet radiation.

5. The method of claim 1 wherein polymerizing the grafting component of comprises irradiating the grafting component with electron beam radiation.

6. The method of claim 1 wherein the binding component is selected from the group consisting of polyaziridine and polycarbodiimide resin compounds when the compound functional groups are carboxyl groups.

7. The method of claim 6 including exposing the coating on the medical device to a basic solution, so that free carboxyl groups on the top coat compound are neutralized.

8. The method of claim 1 wherein the binding component is an aldehyde compound when the top coat compound functional groups are amine groups.

9. The method of claim 1 wherein the binding component is an isocyanate compound when the top coat compound functional groups are selected from the group consisting of hydroxy and amine groups.

10. A method of providing a hydrophilic coating for an intracorporeal medical device, comprising:

a) applying to the medical device a solution, comprising a hydrophilic compound, an ionic compound with at least one inorganic ion, and a grafting component selected from the group consisting of vinyl, acrylate and allyl compounds;

b) polymerizing and crosslinking the grafting component in the presence of the ionic compound, so that the grafting component is crosslinked with the hydrophilic compound in a crosslinked network, to form a hydrophilic coating on the medical device; and c) exposing the hydrophilic coating to a solvent and dissolving the ionic compound in the solvent.

11. The method of claim 10 wherein (c) comprises dissolving the ionic compound in water.

12. The method of claim 10 including before step (a) coating a metal medical device with a primer selected from the group consisting of acrylate, vinyl and allyl compounds, and polymerizing the primer, so that the grafting component binds to the primer to bond to the device.

13. The method of claim 10 including forming the solution of step (a) by combining the hydrophilic compound and the grafting component with an aqueous solution of the ionic compound with at least one inorganic ion.

14. A method of providing a coating for an intracorporeal medical device, comprising:

a) applying to the medical device a solution having a grafting component and a binding component, wherein the grafting component is selected from the group consisting of vinyl, acrylate and allyl compounds, and the binding component is selected from the group consisting of aldehyde compounds, and isocyanate compounds;

b) polymerizing the grafting component, and bonding the grafting component with the binding component, to form a base coat on the device; and c) applying to the base coat a solution of a top coat compound having a functional group capable of bonding to the binding component so that the top coat compound bonds to the binding component to form the coating on the medical device, wherein the binding component is an aldehyde compound when the top coat compound functional group is an amine group and the binding component is an isocyanate compound when the top coat compound functional group is an hydroxy group or an amine group.

15. An intracorporeal medical device having a coating, the coating comprising:

a) a polymerized base coat on the device formed from a solution of a binding component and a grafting component polymerized and crosslinked to the binding component on the device so that the grafting component bonds to the device,
  the binding component being selected from the group consisting of polyaziridine resin compounds, polycarbodiimide resin compounds, aldehyde compounds, and isocyanate compounds and
  the grafting component being selected from the group consisting of vinyl, acrylate and allyl compounds; and b) a top coat on the base coat, comprising a compound having a functional group capable of reacting with the binding component, said functional group selected from the group consisting of carboxyl groups, hydroxy groups and amine groups, bonded to the binding component.

16. The coated device of claim 15 wherein the device is a metal guidewire having a primer coating selected from the group consisting of vinyl, acrylate and allyl compounds.

17. The coated device of claim 15 wherein the binding component is selected from the group consisting of polyaziridine and polycarbodiimide resin compounds when the compound functional groups are carboxyl groups.

18. The coated device of claim 17 wherein the compound is a hydrophilic polymer selected from the group consisting of polyacrylic acid, alginic acid, carboxy methyl cellulose, and hyaluronic acid.

19. The coated device of claim 15 wherein the binding component is selected from the group consisting aldehyde compounds and isocyanate compounds when the compound functional group is an amine group.

20. The coated device of claim 19 wherein the compound is a hydrophilic compound comprising:

a (co)monomer selected from the group consisting of 2-aminoethyl acrylate, 2-aminoethyl methacrylate, N-(3-aminopropyl) methacrylamide;

a polymer of at least one of said (co)monomers co-polymerized with hydrophilic monomers selected from the group consisting of acrylamide, dimethyl acrylamide, and N-vinyl pyrrolidone;

a peptide having a secondary basic group for reaction with the binding component; or polyethylenimine.

21. The coated device of claim 19 wherein the binding component is selected from the group consisting of biuret and isocyanate trimer of 1,6 hexamethylene di-isocyanate.

22. The coated device of claim 19 wherein the binding component is glutaraldehyde.

23. The coated device of claim 15 wherein the binding component is an isocyanate compound when the compound functional group is a hydroxy group.

24. The coated device of claim 23 wherein the compound is a hydrophilic compound selected from the group consisting of poly(vinyl alcohol), hydroxy propyl cellulose, and poly(acrylamide cohydroxy ethyl methacrylate).

25. The coated device of claim 15 wherein the grafting component is trimethylol propane triacrylate.

26. The coated device of claim 15 wherein the device is a polymeric catheter.

27. An intracorporeal medical device having a hydrophilic coating, the coating comprising:

a) a hydrophilic compound; and b) an ionic compound with at least one inorganic ion, dissolvably removable from the hydrophilic coating; and c) a polymerized grafting component selected from the group consisting of vinyl, acrylate, and allyl compounds, crosslinked to the hydrophilic compound in a crosslinked network, the crosslinked network comprising the grafting component polymerized and crosslinked in the presence of the ionic compound.

28. The coated device of claim 27 wherein the hydrophilic compound is selected from the group consisting of poly (ethylene oxide), poly(vinylpyrrolidone), poly(vinyl alcohol), poly(acrylamide), alginic acid, hyaluronic acid, poly(acrylic acid), and guar gum.

29. The coated device of claim 27 wherein the grafting component is trimethylol propane triacrylate.

30. The coated device of claim 27 wherein the device is a metal guidewire having a primer coating selected from the group consisting of acrylate, vinyl, and allyl compounds.

31. The coated device of claim 27 wherein the device is a polymeric catheter.

32. The coated device of claim 27 wherein the coating further includes an ionic compound with at least one inorganic ion.

33. A catheter having a hydrophilic coating, the coating comprising:
   a) a hydrophilic compound;
   b) an ionic compound with at least one inorganic ion, dissolvably removable from the hydrophilic coating; and
   c) a polymerized grafting component selected from the group consisting of vinyl, acrylate and allyl compounds, bonded to the device and crosslinked to the hydrophilic compound into a crosslinked network, the crosslinked network comprising the grafting component polymerized and crosslinked in the presence of the ionic compound.

34. A catheter having a hydrophilic coating, the coating comprising:
   a) a polymerized base coat on the catheter formed from a solution of a binding component and a grafting component polymerized and crosslinked to the binding component on the catheter so that the grafting component bonds to the catheter,
      the binding component being selected from the group consisting of polyaziridine resin compounds, polycarbodiimide resin compounds, aldehyde compounds, and isocyanate compounds and
      the grafting component being selected from the group consisting of vinyl, acrylate and allyl compounds; and
   b) a top coat on the base coat, comprising a compound having a functional group capable of reacting with the binding component, said functional group selected from the group consisting of carboxyl groups, hydroxy groups and amine groups, bonded to the binding component.

35. An intracorporeal medical device having a coating, the coating comprising:
   a) a polymerized base coat on the device, comprising:
      a binding component selected from the group consisting of polyaziridine resin compounds, polycarbodiimide resin compounds, aldehyde compounds, and isocyanate compounds; and
      a grafting component bonded to the binding component, the grafting component being trimethylol propane triacrylate; and
   b) a top coat on the base coat, comprising a compound having a functional group capable of reacting with the binding component, said functional group selected from the group consisting of carboxyl groups, hydroxy groups and amine groups, bonded to the binding component.

36. An intracorporeal medical device having a coating, comprising:
   a) a metal guidewire having a primer coating; and
   b) a coating on the primer coated metal guidewire, comprising:
      i) a polymerized base coat, comprising:
         a binding component selected from the group consisting of polyaziridine resin compounds, polycarbodiimide resin compounds, aldehyde compounds, and isocyanate compounds; and
         a grafting component selected from the group consisting of vinyl, acrylate and allyl compounds, bonded to the binding component; and
      ii) a top coat on the base coat, comprising a compound having a functional group capable of reacting with the binding component, said functional group selected from the group consisting of carboxyl groups, hydroxy groups and amine groups, bonded to the binding component.

37. The medical device of claim 36 wherein the primer coating is selected from the group consisting of vinyl, acrylate and allyl compounds.

38. An intracorporeal medical device having a coating, the coating comprising:
   a) a polymerized base coat on the device, comprising:
      a binding component selected from the group consisting of aldehyde compounds, and isocyanate compounds; and
      a grafting component selected from the group consisting of vinyl, acrylate and allyl compounds, bonded to the binding component; and
   b) a top coat on the base coat, comprising a compound having a functional group capable of reacting with the binding component, bonded to the binding component, wherein the binding component is an aldehyde compound when the top coat compound functional group is an amine group and the binding component is an isocyanate compound when the top coat compound functional group is an hydroxy group or an amine group.

39. An intracorporeal medical device having a hydrophilic coating, comprising
   a) a metal guidewire having a primer coating; and
   b) a coating on the primer coated metal guidewire, comprising:
      i) a hydrophilic compound; and
      ii) a polymerized grafting component selected from the group consisting of vinyl, acrylate, and allyl compounds, crosslinked to the hydrophilic compound in a crosslinked network.

40. The medical device of claim 39 wherein the primer coating is selected from the group consisting of vinyl, acrylate and allyl compounds.

* * * * *